United States Patent [19]

Sottini et al.

[11] Patent Number: 4,842,390

[45] Date of Patent: Jun. 27, 1989

[54] FIBER OPTIC DEVICE FOR ANGIOPLASTY

[75] Inventors: Stefano Sottini, Caldine-Florence; Vera Russo, Florence; Filippo Crea, Roma; Giancarlo Margheri, Florence, all of Italy

[73] Assignee: Consiglio Nazionale Delle Ricerche, Viale Liegi, Italy

[21] Appl. No.: 219,192

[22] Filed: Jul. 15, 1988

[30] Foreign Application Priority Data

Jul. 17, 1987 [IT] Italy .................................. 84143 A/87

[51] Int. Cl.$^4$ ........................... G02B 6/36; G02B 6/02; A61B 1/00
[52] U.S. Cl. .............................. 350/96.15; 350/96.10; 350/96.26; 128/5
[58] Field of Search .... 350/96.10, 96.15, 96.24–96.26, 350/96.18; 128/4–6

[56] References Cited

U.S. PATENT DOCUMENTS

| 4,516,022 | 5/1985 | Lindgren | 350/96.10 X |
| 4,617,926 | 10/1986 | Sutton | 350/96.10 X |
| 4,660,925 | 4/1987 | McCaughan, Jr. | 350/96.15 |
| 4,678,268 | 7/1987 | Russo et al. | 350/96.18 |
| 4,733,937 | 3/1988 | Lia et al. | 350/432 |
| 4,740,047 | 4/1988 | Abe et al. | 350/96.15 |

Primary Examiner—William L. Sikes
Assistant Examiner—Akm E. Ullah
Attorney, Agent, or Firm—Hoffman, Wasson, Fallow & Gitler

[57] ABSTRACT

A fiber optic device for the transmission and lateral irradiation of laser energy, particularly for angioplasty, comprising at least one optical fiber (1), to the inlet end of which there is coupled a laser source (4) and to the outlet end of which, after removing its coating (3), there is applied a microcapsule (5) which is transparent to laser radiation and has a substantially toroidal thickened portion (6) surrounding said end and arranged to give rise to a "corolla-shaped" output laser beam.

14 Claims, 2 Drawing Sheets

FIBER OPTIC DEVICE FOR ANGIOPLASTY

BACKGROUND OF THE INVENTION

This invention relates to a fiber optic device for the transmission and lateral irradiation of laser energy, particularly for angioplasty.

Angioplasty is used in the medical field for removing arteriosclerotic plaques and similar obstructions which form in the arteries, in particular the coronary arteries.

Angioplasty is currently effected by various methods, some of which involve operating from within the artery itself.

One of these known methods comprises the use of a catheter provided at its end with a small inflatable ball. The catheter with the deflated ball is inserted into the artery and advanced until the ball reaches the obstacle to be removed. The ball is then inflated and as i expands, it recanalizes the obstructed vessel. This method has serious drawbacks (see Nigel Sinclair et al, *S.P.I.E.*, vol. 713, page 70, September 1986). In particular, rather than remove the obstruction, this method tends to widen the artery at that particular location. This means that the beneficial effects are only temporary, as the obstruction forms again after a short time.

For these reasons particular attention has been given to laser techniques, which, because of the high energy concerned, are able to destroy and thus definitively eliminate arteriosclerotic plaques.

A known technique is to insert into the artery an optical fiber with a sapphire tip, which emits a laser beam able to destroy the arteriosclerotic plaque facing it.

Drawbacks of this known technique include on the one hand the large size of the sapphire tip, which means that the apparatus can be used only for peripheral large-diameter blood vessels, and on the other hand the risk of perforating the artery wall should this face the laser beam emitted from the sapphire tips as from any conventional fiber tip.

To obviate these drawbacks it has been proposed to use a fiber optic probe with the laser outlet covered by a metal tip. The tip is heated by the laser beam and is moved forward so that it burns the arteriosclerotic plaque.

The main drawback of this technique is the loss of the potential advantages of the laser source, which in this case is used only to heat the metal tip as in the case of a normal source of electricity, so losing the selective effect of the laser beam on the arteriosclerotic plaque relative to the surrounding healthy tissue.

A further drawback is that the hot tip can adhere to the tissue with the risk of damage.

SUMMARY OF THE INVENTION

These drawbacks are obviated according to the invention by a fiber optic device for the transmission and lateral irradiation of laser energy, particularly for angioplasty, characterized by comprising at least one optical fiber, to the inlet end of which there is coupled a laser source and to the outlet end of which, after removing its coating, there is applied a microcapsule which is transparent to laser radiation and has a substantially toroidal thickened portion surrounding said end and arranged to give rise to a "corolla-shaped" output laser beam.

BRIEF DESCRIPTION OF THE DRAWINGS

Some embodiments of the present invention are described in detail hereinafter with reference to the accompanying drawings, in which.

DETAILED DESCRIPTION OF THE PREFERRED EMBODIMENT

Figure 1:
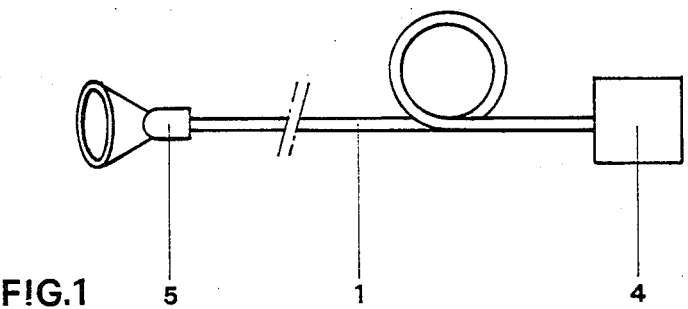
FIG. 1 is a diagrammatic view of a device according to the invention.

As can be seen from the figures, the device according to the invention consists essentially of an optical fiber 1 which in the illustrated example comprises a quartz core 2 of 200–300 $\mu$m diameter and a plastic coating 3.

The inlet end of the fiber 1 is coupled in conventional manner to a laser source 4, whereas the outlet end, after the plastic coating has been removed, is housed in a microcapsule 5 constructed of a material transparent to laser radiation, such as quartz.

The microcapsule 5, which consists preferably of a piece of capillary closed at one end, has at that end an annular thickened portion 6 formed when the end of the quartz capillary is fused for the purpose of closing it.

The shape of this annular thickened portion and thus the optical characteristics of the system can be varied by varying the capillary heating time and the possible mechanical stressing exerted during heating, as will be clarified hereinafter.

The microcapsule 5 is fixed to the plastic coating 3 by a collar 7 of sealing material which, besides providing a fluid-tight seal between the two pieces, also fixes the end of a capillary 8 which extends external to the microcapsule 5 parallel to the optical fiber 1 and is enclosed together with this latter within single Teflon sheath 9.

The operation of the device according to the invention is as follows:

The laser radiation, generated by the source 4 and transferred along the fiber, reaches the coating-free end 3 and emerges as a divergent beam. The angle of divergency depends essentially in known manner on the numerical aperture of the fiber and the fiber-source coupling. The emerging beam encounters the annular thickened portion 6 and as the thickness of this varies from its center to its periphery, it behaves substantially as a lens of approximately toroidal shape, which has the effect of radiating a "corolla-shaped" laser beam, that is of radiating the laser light approximately along the generators of a substantially conical surface, as illustrated diagrammatically in FIG. 2. The width of the cone depends on the extent of the converging effect of the annular thickened portion 6 and on the optical characteristics of the fiber used.

Figure 2:
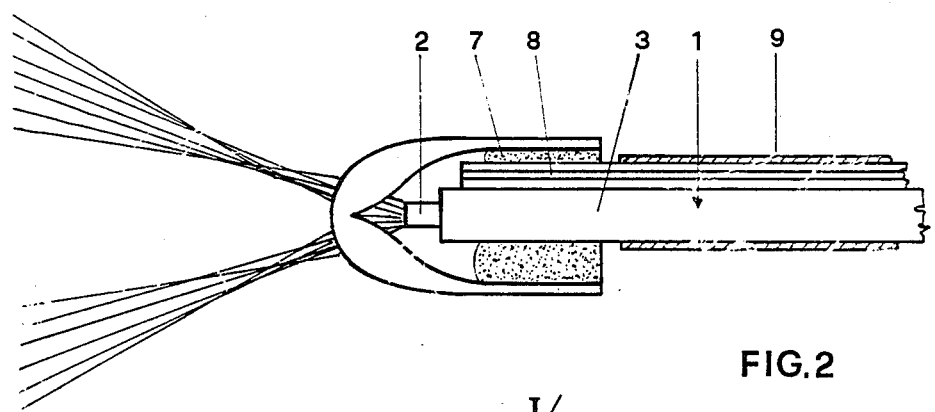
FIG. 2 is a longitudinal section through a first embodiment of the outlet and of the optical fiber covered with the microcapsule.
Figure 3:
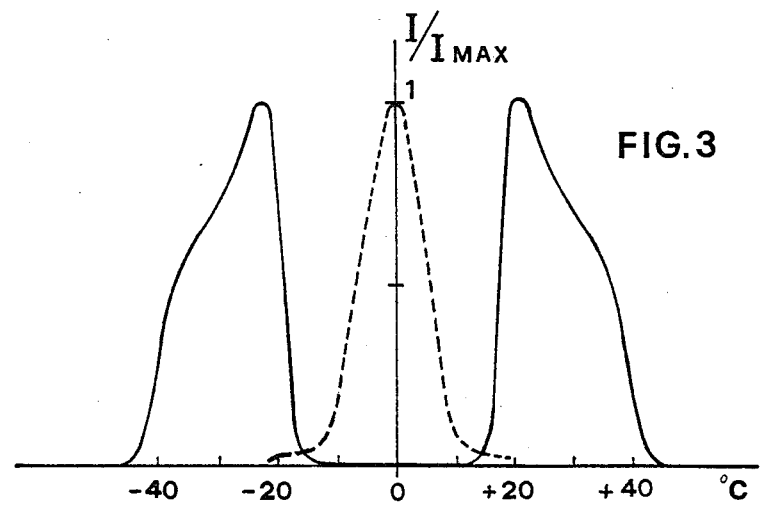
FIG. 3 shows the radiation diagram of the device of FIG. 2.

FIG. 3 shows the radiation diagram for the optical fiber of FIG. 2 (full line) in which the outlet and surface of the core 2 is cut orthogonally to the fiber axis. As can be seen from this radiation diagram, in which the horizontal axis represents the angle to the fiber axis and the vertical axis represents the emission intensity in the direction corresponding to these angles, the laser energy emitted by the fiber end collects on a conical surface symmetrical about the fiber axis and having a cone angle of about 20°.

The width of the two peaks (about 6°) gives an idea of the collimation effect obtained. For comparison purposes the dashed line shows the analogous radiation diagram for the same optical fiber as FIG. 2 but without the microcapsule.

In use, the fiber with the microcapsule is inserted into the artery to be treated and is advanced along it so that the collimated laser beam reaches the side wall of the artery to destroy the obstructions encountered during its advancement.

It is apparent that the described device is particularly advantageous in angioplasty in that:

the microcapsule 5 has a shape which combines considerable mechanical strength with the facility for easy movement along the artery without causing any damage to it;

the optical system obtained ensures absolute absence of radiation in the direction of the fiber axis, so minimizing the risk of damaging the artery especially at bends and bifurcations, at which the danger of piercing the facing wall is greatest;

the shape of the radiated beam is particularly suited to destroying the arteriosclerotic plaques circularly associated with the artery wall.

As stated, the shape of the thickened portion, the type of fiber, the shape of the outlet end of the core and its position in the microcapsule determine the optical characteristics of the system.

Figure 4:
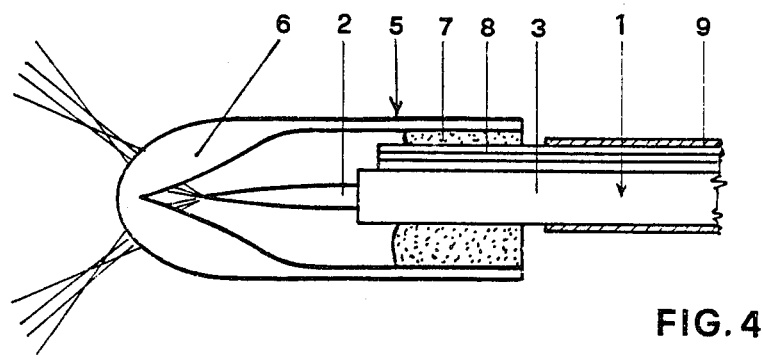
FIG. 4 is a longitudinal section through a second embodiment of the outlet end of the optical fiber.
Figure 5:
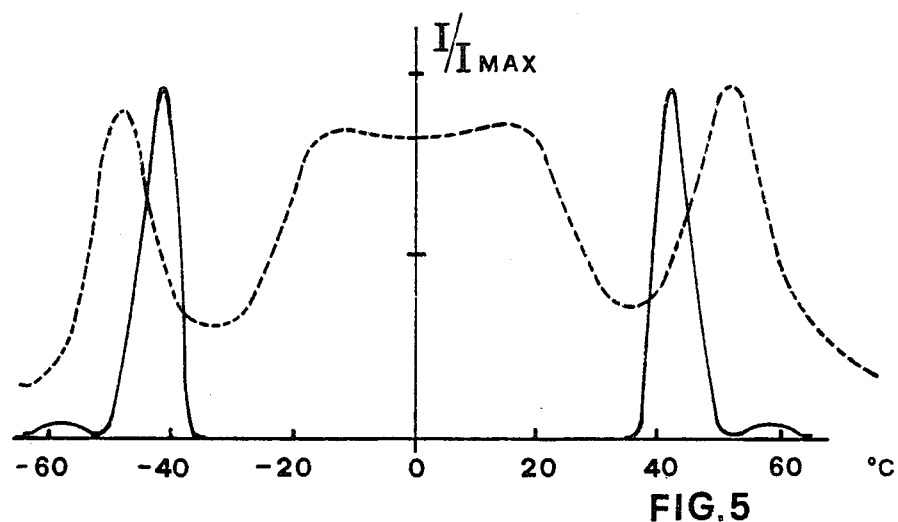
FIG. 5 shows the radiation diagram of the device of FIG. 4.
Figure 6:
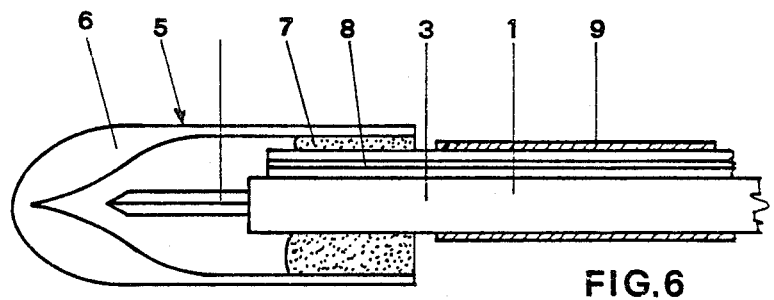
FIG. 6 is a longitudinal section through the outlet and of multiple optical fiber.

For example, the optical fiber core of the device shown in FIG. 4 has a conical outlet end. This (see Chang and Aauth, *J.O.S.A.*, vol. 68, No. 9, Sept. 1978; Russo et al, *S.P.I.E.*, vol. 492, 1986) determines a greater divergence of the radiation leaving the end and encountering the thickened portion 6, which then generates a light cone of greater width, as shown in the radiation diagram of FIG. 5. In this, the full line represents the radiation diagram when the microcapsule 5 is present, and the dashed line the radiation diagram without the microcapsule. Again in this case, the collimation effect introduced by the microcapsule can be evaluated by noting the different length of the peaks on the two curves, these being about 16° for the conical end without microcapsule (dashed line) and about 6° for the conical end with microcapsule (full line).

In both the embodiments shown, the optical fiber outlet end is coaxial to the microcapsule 5. If, however, the fiber outlet end is not aligned with or can be moved out of alignment with the microcapsule 5, the light cone leaving said microcapsule, although having the same cone angle determined essentially by the shape of the thickened portion 6, has a non-uniform light intensity distribution within the beam.

The same non-uniform light distribution effect in the beam can be obtained by using instead of a single fiber a multiple fiber in which individual fibers are distributed in a uniform ring arrangement (Kapany—*Fibre Optical: Principles and Applications*, Academic Press, Ch. 5, 1967). In this way the conical light surface leaving the microcapsule 5 is obtained by the addition of several sectors, for each of which the energy contribution is given by one fiber. It is apparent that on varying the degree of coupling between the source and each fiber at the inlet end, the light distribution in the conical surface also varies. The methods for varying the source-fiber coupling efficiency are known and do not represent part of the invention.

In practice, during the use of the device, the high energy available generates heat within the microcapsule 5, together with a dangerous pressure increase in the gas or air contained in the microcapsule. This pressure excess can be eliminated through the capillary 8. Alternatively, it is possible to create a vacuum in the microcapsule 5, although this requires a more laborious and costly construction.

A further simpler method is to make a small hole in the microcapsule 5 through which the gas can vent to the outside.

This method is, however, not valid in the case of angioplasty as themicrocapsule generally operates surrounded by blood which could then enter its interior, resulting in inevitable blood damage at least if intense radiation is present.

We claim:

1. A fiber optic device for the transmission and lateral irradiation of laser energy, particularly for angioplasty, characterized by comprising at least one optical fiber (1), to the inlet end of which there is coupled a laser source (4) and to the outlet end of which, after removing its coating (3), there is applied a microcapsule (5) which is transparent to laser radiation and has a substantially toroidal thickened portion (6) surrounding said end and arranged to give rise to a "corolla-shaped" output laser beam further comprising sealing means interposed between the outer lateral surface of the optical fiber (1) and the inner lateral surface of the microcapsule (5).

2. A device as claimed in claim 1, characterized in that the optical fiber (1) is of single type.

3. A device as claimed in claim 1, characterized in that the optical fiber (1) is of multiple type.

4. A device as claimed in claim 1, characterized in that the outlet end of the optical fiber (1), is cut orthogonal to the fiber axis.

5. A device as claimed in claim 1, characterized in that the outlet end of the optical fiber (1) is of conical shape.

6. A device as claimed in claim 3, characterized in that the efficiency of the coupling between the laser source (4) and each element of the multiple optical fiber (1) is adjustable.

7. A device as claimed in claim 1, characterized in that the microcapsule (5) consists of a portion of capillary sealed at one end.

8. A device as claimed in claim 1, wherein the sealing means is a collar of sealing material.

9. A device as claimed in claim 1, characterized in that the interior of the microcapsule (5) is under vacuum.

10. A device as claimed in claim 1, characterized by comprising an aperture for communication between the interior cavity of the microcapsule (5) and the outside.

11. A device as claimed in claim 10, characterized by comprising a capillary (8) which connects the interior cavity of the microcapsule (5) to the outside.

12. A device as claimed in claim 11, characterized in that the optical fiber (1) and the capillary (8) are contained in a single sheath (9).

13. A device as claimed in claim 11, characterized in that the end of the fiber (1) within the microcapsule (5) is adjustable axially.

14. A device as claimed in claim 11, characterized in that the end of the fiber (1) within the microcapsule (5) is adjustable transversely.

* * * * *